United States Patent [19]

Baldwin et al.

[11] Patent Number: 4,567,191

[45] Date of Patent: Jan. 28, 1986

[54] AMINO-PHENYL-THIADIAZOLEDIOXIDES AS GASTRIC SECRETION INHIBITORS

[75] Inventors: John J. Baldwin, Gwynedd Valley; Adolph Pietruszkiewicz, North Wales; William A. Bolhofer, Frederick; William C. Lumma, Jr., Pennsburg, all of Pa.

[73] Assignee: Merck & Co., Inc., Rahway, N.J.

[21] Appl. No.: 501,943

[22] Filed: Jun. 7, 1983

[51] Int. Cl.$^4$ .................. C07D 285/10; C07D 417/12; A61K 31/41

[52] U.S. Cl. ..................................... 514/362; 514/274; 514/342; 544/238; 544/315; 546/277; 548/134; 548/135

[58] Field of Search ................. 548/135, 134; 546/277; 544/238, 315; 514/362, 342, 274

[56] References Cited

U.S. PATENT DOCUMENTS

| | | | |
|---|---|---|---|
| 3,950,333 | 4/1976 | Durant | 260/250 |
| 4,128,658 | 12/1978 | Price | 424/285 |
| 4,362,728 | 12/1982 | Yellin | 424/249 |
| 4,411,899 | 10/1983 | Baldwin | 424/246 |

FOREIGN PATENT DOCUMENTS

| | | | |
|---|---|---|---|
| 867106 | 11/1978 | Belgium | 548/135 |
| 875846 | 10/1979 | Belgium | 548/135 |
| 40096 | 12/1981 | European Pat. Off. | 548/135 |
| 67436 | 12/1982 | European Pat. Off. | 548/135 |
| 99121 | 1/1984 | European Pat. Off. | 548/135 |
| 2124622 | 2/1984 | United Kingdom | 548/135 |

OTHER PUBLICATIONS

Lumma et al., J. Med. Chem. 27 1047 (1984).

*Primary Examiner*—Robert Gerstl
*Attorney, Agent, or Firm*—Gabriel Lopez; Hesna J. Pfeiffer; Daniel T. Szura

[57] ABSTRACT

Novel amino-phenyl-thiadiazoledioxides and related compounds and processes for preparing such compounds are disclosed. The compounds are useful for suppressing gastric acid secretions in mammals.

7 Claims, No Drawings

AMINO-PHENYL-THIADIAZOLEDIOXIDES AS GASTRIC SECRETION INHIBITORS

BACKGROUND OF THE INVENTION

Inhibitors of gastric acid secretion functioning by antagonism of the histamine H2-receptor are effective antiulcer agents. Structurally, such compounds are typically viewed as molecules having three substituents or fragments; i.e., A-B-C, each of which can independently affect the antisecretory activity. The "A" portion may be a substituted or unsubstituted aromatic or heteroaromatic group such as are disclosed in, for example, U.S. Pat. No. 3,950,333 to Durant et. al., U.S. Pat. No. 4,128,658 to Price et. al., and Belgian Pat. Nos. 867,106 and 875,846 (Derwent Abstracts 84065A/47 and 79110B/44, respectively).

The central, or "B" portion, may be a connecting chain joined to A such as A—CH$_2$SCH$_2$CH$_2$—, AOCH$_2$CH$_2$CH$_2$, and the like.

The remaining terminal substituent "C" is structurally distinct from either the A or B portions and may be, for example, a substituted guanidine, a substituted 1,1-diamino ethylene, or a 3,5-diamino-1-alkyl triazole as disclosed in the aforementioned U.S. Patents to Durant et. al., and Price et. al., as well as in Belgian Pat. No. 875,846.

The present invention is directed to unique "C" moieties which confer antisecretory activity when combined with the A-B molecular fragments comprising these antiulcer agents. These novel "C" moieties, i.e., amino-phenyl-thiadiazoledioxides, when incorporated into the A-B molecular fragments, afford compounds that exhibit gastric antisecretory activity.

SUMMARY OF THE INVENTION

This invention is directed to amino-phenyl-thiadiazoledioxides and related compounds as well as intermediates and processes for the preparation of such compounds.

DESCRIPTION OF THE INVENTION

The compounds of this invention are represented by the following structural formula:

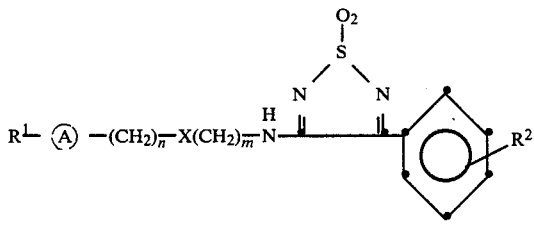

wherein R$^1$ is hydrogen, loweralkyl,

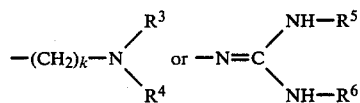

wherein

R$^3$ and R$^4$ are independently hydrogen, loweralkyl, cycloloweralkyl or phenylloweralkyl or R$^3$ and R$^4$ may be joined to form, along with the nitrogen to which they are attached, a 5- or 6-membered heterocycle, which may also contain an oxygen, sulfur, SO, SO$_2$, or an N→R$^7$ linkage wherein R$^7$ is hydrogen or loweralkyl of from 1 to 3 carbon atoms;

R$^5$ and R$^6$ are independently hydrogen, loweralkyl, or 3,3,3-trifluoroethyl or R$^5$ and R$^6$ may be joined together to form a cyclic structure through a —(CH$_2$)$_m$-linkage;

n is 0 or 1;

m is 2 to 4;

k is 0 to 4;

X is oxygen, sulfur or methylene:

R$^2$ is hydrogen, halogen, loweralkyl, or loweralkoxy;

Ⓐ is phenylene or a 5- or 6-membered heterocycle containing one to three heteroatoms selected from oxygen, sulfur or nitrogen, which may optionally have a benzo ring fused thereon provided that when Ⓐ is a 5-membered heterocycle, or a benzo-fused 5-membered heterocycle containing one heteroatom, n is 1;

and, the physiologically acceptable salts and N-oxides thereof.

Examples of Ⓐ in Formula I are furan, thiophene, pyrrole, oxazole, oxadiazole, thiadiazole, thiazole, triazole, pyrazole, imidazole, pyridine, pyrimidine, pyrazine, and the like and the fused benzo derivatives thereof such as benzofuran, benzoxazole, benzimidazole, and the like.

Examples of the 5- or 6-membered heterocycles represented by R$^3$ and R$^4$ when joined are pyrrolidino, piperidino, morpholino, thiomorpholino, piperazine, and N-loweralkyl piperazino.

Useful intermediates for the preparation of compounds of Formula I are those compounds of the formula

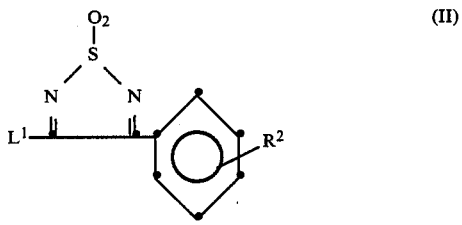

wherein

L$^1$ is amino, hydroxy, or a leaving group such as loweralkoxy, aryloxy, loweralkylthio, loweralkyl-sulfonyl, arylthio, arylsulfonyl, halo, and the like, and R$^2$ is defined above, In the instant invention, unless specified otherwise, the term "loweralkyl" is intended to include those alkyl groups containing from 1 to 5 carbon atoms in either a straight or branched configuration. Examples of such alkyl groups are methyl, ethyl, propyl, iso-propyl, butyl, sec-butyl, pentyl, and the like.

The term "cycloloweralkyl" is intended to include those cycloalkyl groups of from 3 to 7 carbon atoms. Examples of such cycloalkyl groups are cyclopropyl, cyclobutyl, cyclopentyl, cyclohexyl, and cycloheptyl.

By "halogen" is meant Fl, Cl, Br, and I.

Preferred compounds of the invention are realized when R$^3$ and R$^4$ are independently hydrogen, loweralkyl, cycloloweralkyl or when R$^3$ and R$^4$ are joined to form a piperidine heterocyclic ring.

Further such preferred compounds are those wherein Ⓐ is m-phenylene or a 6-membered heterocycle as defined above, n is 0, X is oxygen, m is 3 and R¹ is:

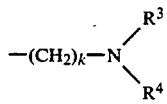

In such cases it is further preferred that k be 1 and R³ and R⁴ be loweralkyl, preferably methyl, or joined to form a morpholine, thiomorpholine, thiomorpholine S-oxide, thiomorpholine S-dioxide, piperidine, or N-loweralkyl piperazine heterocyclic ring.

Additional preferred variations of Ⓐ are those wherein Ⓐ is furan, imidazole, thiazole, oxazole, thiophene, triazole, thiadiazole, oxadiazole, or benzofuran.

When Ⓐ is a heterocycle containing one heteroatom, it is preferred that n=1, X=sulfur, and m=2.

The preferred values of R¹ will depend upon and vary with the definition of Ⓐ. When Ⓐ is furan or benzofuran, R¹ is preferred to be:

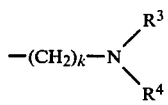

wherein it is further preferred that k=1 and R³ and R⁴ be hydrogen or loweralkyl, preferably hydrogen or methyl, or joined to form a morpholine, thiomorpholine, piperidine, or N-methyl piperazine ring.

When Ⓐ is thiazolyl, R is preferably

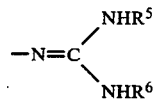

wherein R⁵ and R⁶ are most preferably hydrogen.

Many of the compounds according to the invention readily form physiologically acceptable salts. Such salts include salts with inorganic acids such as hydrochlorides, hydrobromides, sulfates, nitrates and phosphates. Particularly useful salts of organic acids are formed with aliphatic mono- or dicarboxylic or sulfonic acids. Examples of such salts are acetates, maleates, fumarates, tartrates, citrates, benzoates, succinates, methane sulfonates, and isethionates. The compounds and their salts may also form hydrates and solvates. In addition, the nitrogen atoms in groups R¹ and Ⓐ, may also form quaternary salts and N-oxides. Such derivatives are also deemed to be included in the compounds of the present invention.

All of the various tautomeric structures of the instant compounds are intended to be included in this invention. In addition, when R¹ is guanidino, three tautomers are possible as determined in the art, and all such tautomers are included in this invention.

The compounds of this invention have been found to have pharmacological activity in the animal body as antagonists to certain actions of histamine which are not blocked by "antihistamines" such as mepyramine. For example, they inhibit selectively the histamine-stimulated secretion of gastric acid in the stomach of chronic fistula dogs at doses of from 0.01 to 10 mg per kilogram intravenously or orally from 0.1 to 500 mg per kilogram. Similarly, the action of these compounds is demonstrated by their antagonism to the effects of histamine on other tissues which are not affected by histamine Hl antagonists. An example of such tissue is the isolated guinea-pig right atrium.

The pharmaceutical carrier employed may be, for example, either a solid or liquid. Exemplary of solid carriers are lactose, terra alba, sucrose, talc, gelatin, agar, pectin, acacia, magnesium stearate, stearic acid and the like. Exemplary of liquid carriers are syrup, peanut oil, olive oil, water and the like.

A wide variety of pharmaceutical forms can be employed. Thus, if a solid carrier is used, the preparation can be tableted, placed in a hard gelatin capsule in powder or pellet form, or in the form of a troche or lozenge. The amount of solid carrier will vary widely but preferably will be from about 15 mg to about 0.4 gm. If a liquid carrier is used, the preparation may be in the form of a syrup, emulsion, soft gelatin capsule, sterile injectable liquid such as an ampoule, or an aqueous or nonaqueous liquid suspension.

The pharmaceutical compositions are prepared by conventional techniques involving procedures such as mixing, granulating and compressing or dissolving the ingredients as appropriate to obtain the desired preparation.

The active ingredient will be present in the composition in an amount effective to inhibit histamine gastric acid secretory activity. The route of administration may be orally or parenterally.

Preferably, each daily dosage will contain the active ingredient in an amount of from about 5 mg to about 1000 mg, most preferably from about 15 mg to about 300 mg given in a single dose or multiple divided doses.

For therapeutic use, the pharmacologically active compounds of the present invention will normally be administered as a pharmaceutical composition comprising at least one such compound as the sole or an essential active ingredient in the basic form or in the form of an addition salt with a pharmaceutically acceptable acid and in association with a pharmaceutical carrier therefor. Such addition salts include those mentioned above.

Other pharmacologically active compounds may, in certain cases, be included in the composition. It may be appropriate to combine the instant compound or compounds with anticholinergic agents such as propantheline; Hl antihistamines such as mepyramine, pyribenzamine, chlorpheniramine and the like; or prostanoids.

Advantageously the composition will be made up in a dosage unit form appropriate to the desired mode of administration such as, for example, a tablet, capsule or injectable solution.

The compounds of this invention can be synthesized by the methods shown in the following Reaction Schemes wherein R¹, R², Ⓐ, X, m and n are as defined above unless otherwise specified and L is an appropriate leaving group such as loweralkoxy, aryloxy, loweralkylthio, loweralkylsulfonyl, arylthio, arylsulfonyl, halo (F, Cl, Br, I), and the like. The aryl- and loweralkyl sulfonyl leaving groups are prepared by oxidation of the corresponding arylthio and loweralkylthio leaving groups as by peroxides or peracids.

REACTION SCHEME I

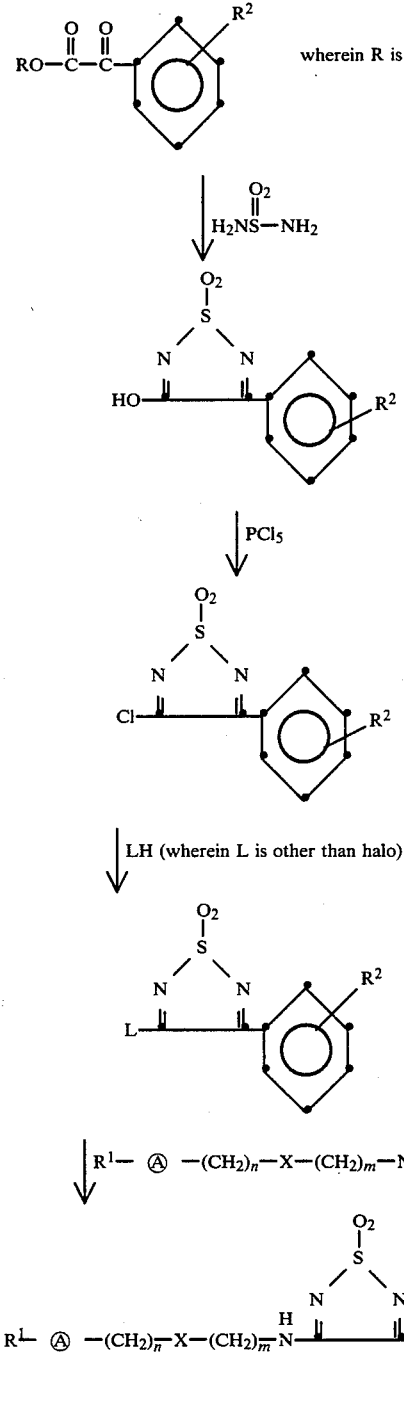

REACTION SCHEME II

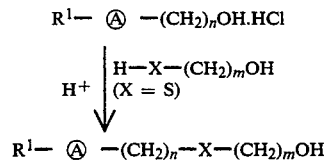

-continued
REACTION SCHEME II

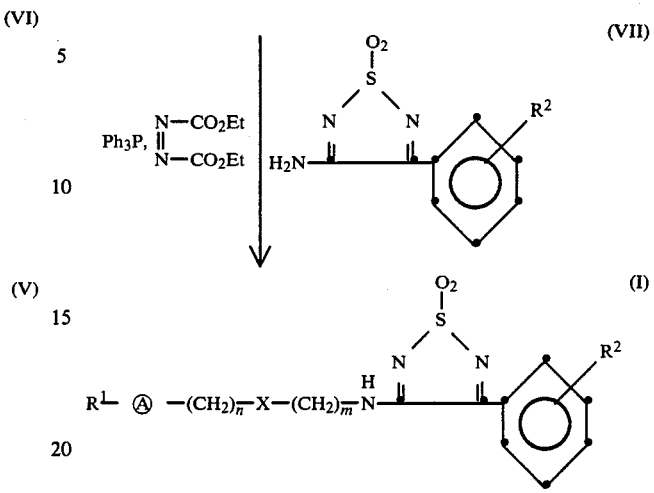

As shown in Reaction Scheme I, a loweralkylphenyl-glyoxylate (VI) is reacted with sulfamide to produce a 3-hydroxy-4-phenyl-thiadiazoledioxide which is then reacted with a phosphorus halide to produce a halo-phenylthiadiazoledioxide (IV) which is itself a compound of Formula II when L is halogen or which can be reacted with a compound of the formula LH wherein L is not halogen or aryl- or alkylsulfonyl to produce a compound of Formula II wherein L is not halogen or aryl- or alkylsulfonyl. The aryl- and loweralkyl sulfonyl leaving groups are prepared by oxidation of the corresponding arylthio and loweralkylthio leaving groups as by peroxides or peracids. Phenylthiadiazoledioxide (II) is then reacted in a polar solvent such as a loweralkanol (e.g., ethanol), N,N-dimethylformamide (DMF), acetonitrile ($CH_3CN$), or tetrahydrofuran (THF) at a temperature of 0° C. to the reflux temperature of the solvent (preferably at ambient temperature) with a complex alkyl amine (III) in essentially equimolar amounts to displace leaving group L and obtain a compound of Formula I.

Alternatively, as seen in Reaction Scheme II, intermediate amine alcohol (VIII) is synthesized from amine alcohol (X) and mercapto alkanol (IX) in the presence of an acid. Intermediate alcohol (VIII) is then activated toward nucleophiles with triphenyl phosphine/diethyl azodicarboxylate or similar reagents in the presence of arylaminothiadiazole dioxide intermediates (VII) to produce compounds of Formula I.

Preferred compounds of Formula I are as follows:

-continued

| R¹ | A | n | X | m | R² |
|---|---|---|---|---|---|
| 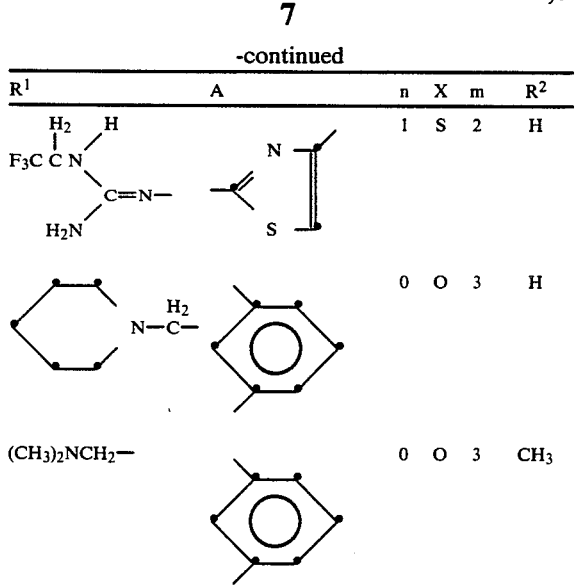 | | 1 | S | 2 | H |
| | N—CH₂— (with cyclohexyl) / phenyl | 0 | O | 3 | H |
| (CH₃)₂NCH₂— | phenyl | 0 | O | 3 | CH₃ |

The following examples are provided to further illustrate the invention, but they are not to be construed as limiting. Unless otherwise indicated, all temperatures are in degrees Celsius.

EXAMPLE 1

3-Hydroxy-4-phenyl-1,2,5-thiadiazole-1,1-dioxide

Sulfamide (4.8 g, 50 mmoles) in ethanol (90 ml) was added slowly with stirring under nitrogen to a solution of sodium (1.15 g, 50 mmoles) dissolved in ethanol (35 ml). The suspension was stirred for 15 minutes at room temperature and then ethyl phenylglyoxylate (8.9 g, 50 mmoles) in ethanol (15 ml) was added. After stirring 15 minutes, the mixture was refluxed overnight and concentrated under vacuum. The residue was suspended in diethyl ether, filtered and the collected solid dissolved in water (25 ml). Acidification with hydrochloric acid precipitated the product which was collected by filtration, washed with water and recrystallized from a mixture of acetonitrile (12 ml) and toluene (8 ml) to obtain 4.2 g (40%) of the title compound, mp 202°–4°. Nmr (DMSO-d₆): δ 7.29–7.89 (m, 3H), 8.19–8.49 (m, 2H).

Anal. Calcd. for $C_8H_6N_2O_3S$: C, 45.71; H, 2.88; N, 13.33. Found: C, 45.71; H, 2.75; N, 13.42.

EXAMPLE 2

3-Ethoxy-4-phenyl-1,2,5-thiadiazole-1,1-dioxide (II)

3-Hydroxy-4-phenyl-1,2-5-thiadiazole-1,1-dioxide, prepared as in Example 1, (1.37 g, 6.5 mmoles) was refluxed with phosphorus pentachloride (3 g, 14.4 mmoles) in methylene chloride (50 ml) for 24 hours. The cooled reaction mixture was added with stirring over 15 minutes to ethanol (50 ml) and then refluxed 1 hour. After concentration under vacuum, the residual solid was suspended in diethyl ether, filtered and recrystallized from ethanol to obtain 1.2 g (78%) of the title compound, mp 204°–6°. Nmr (DMSO, d₆) δ 1.53 (t, 3H, J=7 Hz), 4.71 (q, 2H, J=7 Hz), 7.34–7.83 (m, 3H), 8.07–8.32 (m, 2H).

Anal. Calcd. for $C_{10}H_{10}N_2O_3S$: C, 50.41; H, 4.23; N, 11.76. Found: C, 50.49; H, 4.34; N, 11.82.

EXAMPLE 3

3-Amino-4-phenyl-1,2,5-thiadizaole-1,1-dioxide (VII)

Ammonia in ethanol (5 ml, 1.4N) was added to a suspension of 3-ethoxy-4-phenyl-1,2,5-thiadiazole-1,1-dioxide, prepared as in Example 2, (1.19 g, 51 mmoles) in ethanol (25 ml). The mixture contained in a closed flask was immersed in a sonic bath until solution was effected and then concentrated under vacuum after standing ½ hour. The residue was refluxed in n-butyl chloride (25 ml), the supernatant decanted, and the solid washed with methylene chloride. After recrystallization from ethyl acetate, 0.72 g (73%) of the title compound was obtained, mp 213° (dec). Nmr (DMSO, d₆) δ 7.73 (m, 5H), 8.28 (broad s, 1H), 9.63 (broad s, 1H).

Anal. Calcd. for $C_8H_7N_3O_2S$: C, 45.92; H, 3.37; N, 20.08. Found: C, 46.00; H, 3.46; N, 20.13.

EXAMPLE 4

3-[2-[5-(Dimethylaminomethyl)-2-furanylmethylthio]ethylamino]-4-phenyl-1,2,5-thiadiazole-1,1-dioxide (I)

3-Ethoxy-4-phenyl-1,2,5-thiadiazole-1,1-dioxide (0.834 g, 0.0035M) and 2-[5-(dimethylaminomethyl)-2-furanylmethylthio]ethylamine (0.825 g, 0.00385M) were dissolved in ethanol (5 ml) and stirred at ambient temperature for 24 hours. The reaction mixture was concentrated under vacuum and the residue chromatographed on 125 g silica with a mixture of chloroform, 800 ml, hexane, 400 ml, and methanol, 45 ml. The combined product fractions were concentrated under vacuum to obtain the product oil, 1.3 g, as a chloroform solvate as confirmed by $H^1$ and $C^{13}$ NMR. $C^{13}$ NMR (DMSO, d₆) ppm 28.9, 27.2, 108.3, 109.6, 164.

Anal. Calcd. for $C_{18}H_{23}N_4O_3S_2$. 0.85 $CHCl_3$: N, 11.03; C, 44.56; H, 4.53. Found: N, 10.96; C, 44.68; H, 4.89.

What is claimed is:

1. Compounds having the formula:

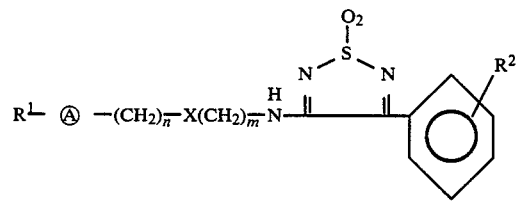

wherein R¹ is hydrogen, loweralkyl,

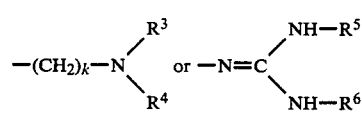

wherein

R³ and R⁴ are independently hydrogen, loweralkyl, cycloloweralkyl or phenylloweralkyl or R³ and R⁴ may be joined to form, along with the nitrogen to which they are attached, a 5- or 6-membered heterocycle, which may also contain an oxygen, sulfur, SO, SO₂, or an N—R⁷ linkage wherein R⁷ is hydrogen or loweralkyl of from 1 to 3 carbon atoms;

R⁵ and R⁶ are independently hydrogen, loweralkyl, or 3,3,3-trifluoroethyl or R⁵ and R⁶ may be joined together to form a cyclic structure through a —(CH$_2$)$_m$-linkage;

n is 0 or 1;

m is 2 to 4;

k is 0 to 4;

X is oxygen, sulfur or methylene:

R$^2$ is hydrogen, halogen, loweralkyl, or loweralkoxy;

Ⓐ is phenylene or a heterocycle selected from furan, thiophene, pyrrole, oxazole, oxadiazole, thiadiazole, thiazole, triazole, pyrazole, imidazole, pyridine, pyrimidine, pyrazine, benzofuran, benzoxazole and benzimidazole, provided that when Ⓐ is a 5-membered heterocycle, or a benzo-fused 5-membered heterocycle containing one heteroatom, n is 1;

and, the physiologically acceptable salts and N-oxides thereof.

2. A compound of claim 1 wherein Ⓐ is furanyl, n=1, X=sulfur, and m=2.

3. A compound of claim 1 which is 3-[2-[5-(dimethylaminomethyl)-2-furanylmethylthio]ethylamino]-4-phenyl-1,2,5-thiadiazole-1,1-dioxide.

4. A compound of claim 1 wherein Ⓐ is meta-phenylene, n=0, X=oxygen, and m=3.

5. A compound of claim 1 wherein R$^1$ is —N=C(NHR$^5$)NHR$^6$, Ⓐ is thiazole, n=1, X=sulfur, and m=2.

6. A pharmaceutical composition useful for suppressing gastric acid secretions in an animal with excess gastric acid secretions which comprises a pharmaceutically inert carrier and an antisecretorily effective amount of a compound of claim 1.

7. A method for suppressing gastric acid secretions in an animal with excess gastric acid secretions which comprises administering to said animal an antisecretorily effective amount of a compound of claim 1.

* * * * *